United States Patent [19]

Alliger et al.

[11] Patent Number: 5,616,347

[45] Date of Patent: Apr. 1, 1997

[54] CHLORINE DIOXIDE SKIN MEDICATING COMPOSITIONS FOR PREVENTING IRRITATION

[76] Inventors: Howard Alliger, 10 Ponderosa Dr., Melville, N.Y. 11747; Habib Roozdar, 9 Rolling Hills Dr., Nesconset, N.Y. 11767

[21] Appl. No.: 388,622

[22] Filed: Feb. 14, 1995

[51] Int. Cl.$^6$ .......................... A01N 59/00; A61K 33/20; A61K 33/40

[52] U.S. Cl. .......................... 424/665; 424/613; 424/615; 424/661; 424/662; 424/663; 424/664; 424/195.1; 514/390; 514/738; 514/922

[58] Field of Search .................. 424/661, 665, 424/662, 663, 664, 613, 615, 195.1; 423/477; 514/738, 390, 922

[56] References Cited

U.S. PATENT DOCUMENTS

| | | | |
|---|---|---|---|
| 4,891,216 | 1/1990 | Kross et al. | 424/661 |
| 4,986,990 | 1/1991 | Davidson et al. | 424/665 |
| 5,407,656 | 4/1995 | Roozdar | 423/477 |

OTHER PUBLICATIONS

The New Encyclopedia Britannica, Encyclopedia Britannica, Inc., Chicago, 15th Edition, 1994, vol. 1, p. 291.

Remington's Pharmaceutical Sciences, Mack Printing Co., Easton(PA), 18th Edition, 1990, p. 773.

*Primary Examiner*—John Pak
*Attorney, Agent, or Firm*—Henry D. Coleman; R. Neil Sudol

[57] ABSTRACT

The present invention relates to the discovery that the inclusion of effective amounts of an irritation reducing compound selected from the group consisting of allantoin, glycerine, aloe vera and mixtures, thereof, in a chlorine dioxide generating composition will substantially reduce skin irritation which is caused by chlorine dioxide exposure to the skin.

21 Claims, No Drawings

CHLORINE DIOXIDE SKIN MEDICATING COMPOSITIONS FOR PREVENTING IRRITATION

FIELD OF THE INVENTION

The present invention relates to chlorine dioxide generating compositions for skin use which contain specific additives which reduce or eliminate irritation to the skin and otherwise do not appreciably reduce the activity of the chlorine dioxide in the composition.

BACKGROUND OF THE INVENTION

Chlorine dioxide ($ClO_2$) has been used experimentally in topical applications for many years. It has been disclosed as being applied as a disinfectant on such skin lesions as acne (Alliger, U.S. Pat. No. 4,084,747, 1978), herpes and fungal infections (Kross, U.S. Pat. No. 4,956,184), to disinfect human skin (Kross, U.S. Pat. No. 4,891,216), for application to general and skin infections (Alliger, U.S. Pat. No. 4,330,531), as a skin cleanser (Brown, U.S. Pat. No. 4,737,307) and antiseptic (Bunyan, U.S. Pat. No. 4,035,483).

One of the major problems in using this type of chemically reactive medication is that in certain instances of application onto a wound or skin, the composition may redden and/or irritate the tissue. This is particularly noticeable in a disease such as acne, or on a diabetic ulcer, where the lesion or the area around it may become red and sensitive.

Although chlorine dioxide is not considered toxic and is non-mutagenic (as is chlorine), it is a strong oxidizing agent which may overcome the body's natural reducing capacity while eliminating infection. This undesirable oxidation reaction may be a reason why chlorine dioxide compositions are still not commercially important as skin or wound disinfectants, nor have they ever become approved drugs—a fact particularly surprising since chlorine dioxide medicaments have been shown to kill all bacteria and viruses in about one minute. The speed of kill is faster than formaldehyde and iodine compounds.

Over the past 15 years a number of additives have been tested with chlorine dioxide generating medicaments in an effort to protect the skin and reduce or eliminate irritation while the lesion is being treated. Two of the more obvious putative solutions to the problem involved the addition of petrolatum and lanolin, since by tradition in topical applications, these agents are highly compatible with body tissue and long considered soothing. These two agents, however, provide little or no oxidative protection, and moreover, reduce the speed of bacterial kill. Other common skin emollients and surface active agents such as mineral oil, caster oil and lecithin were tried. These agents, however, provided little beneficial effect. The inclusion of titanium dioxide and soap also had little, or no, protective effect. Another additive, glyceryl monostearate, actually seemed to worsen the irritation.

Because chlorine dioxide is so highly reactive, many compounds are changed chemically on contact with chlorine dioxide or otherwise influence the reactivity of chlorine dioxide. A number of traditional cosmetic and pharmaceutical additives are not practical for inclusion into chlorine dioxide generating formulations including, for example, urea, vitamins A, C, D or E and oil of lavender, because of chemical incompatibility with chlorine dioxide. Some compounds, for example, metallic compounds, carbohydrates and certain wetting agents, alter the smooth, continuous rate of release of the chlorine dioxide gas from the base material, sodium chlorite and its derivative chlorous acid.

After much experimenting, three additives were unexpectedly discovered that were compatible with the strongly reactive chlorine dioxide and reduced the skin irritation of chlorine dioxide without adversely affecting the pharmacological and antimicrobial activity of chlorine dioxide. These agents are allantoin, glycerine and aloe vera. Although these materials are known in the industry as skin moisturizers, it is quite surprising that these agents would exhibit special protective properties, i.e., reduce skin irritation of chlorine dioxide formulations without affecting the pharmacological and antimicrobial activity of chlorine dioxide solutions.

It is particularly surprising that these agents would reduce skin irritation so well, especially in light of the inactivity of related skin protecting compounds. In point of fact, one of ordinary skill would actually expect fat soluble additives such as lanolin, lecithin and related additives to protect the skin better than allantoin, glycerine and aloe vera, if indeed any additives worked at all. In addition to their skin protecting effect, these materials quite unexpectedly enhance the penetration of chlorine dioxide into the skin.

In experimenting with allantoin, glycerine and aloe vera, it was noted that each of these compounds seemed to speed penetration of the chlorine dioxide medication into the skin. It was first thought that this enhanced penetration might have a deleterious effect in topical applications and perhaps even lead to greater irritation of the area of the skin to which the formulation was applied. The gel form of chlorine dioxide medication, in contrast to the liquid form, can be seen to disappear from the surface of the skin or sore very rapidly. While not being limited by way of theory, it is believed that the penetration enhancement exhibited by compositions of the present invention may actually be related to the protective capacity of the additives.

OBJECTS OF THE INVENTION

It is an object of the present invention to provide compositions and methods for generating chlorine dioxide to be used in topical applications in mammals, especially humans.

It is an additional object of the present invention to provide topical chlorine dioxide generating compositions including solutions and gel formulations using readily available ingredients which may be applied to animal, especially human, skin and which evidence substantially reduced irritation of the skin and/or enhanced penetration of chlorine dioxide in the skin.

These and/or other objects of the present invention may be readily gleaned from a reading of the description of the present invention as set forth in detail hereinbelow.

SUMMARY OF THE INVENTION

The present invention relates to the unexpected discovery that the inclusion of effective amounts of an irritation reducing compound selected from the group consisting of allantoin, glycerine, aloe vera and mixtures, thereof, in a chlorine dioxide generating composition will substantially reduce skin irritation which is caused by chlorine dioxide exposure to the skin in comparison to compositions which do not contain such an irritation reducing component.

Compositions according to the present invention comprise an aqueous soluble salt of chlorite in combination with a protic acid, the salt of chlorite and acid being included in the composition in amounts effective to generate at least about 1 part per million (ppm) of chlorine dioxide within a period of time no greater than about 10 minutes, the composition also including water and at least one irritation reducing compound selected from the group consisting of allantoin, glycerine, aloe vera and mixtures, thereof, in an amount effective to substantially reduce skin irritation caused by chlorine dioxide. The compositions according to the present invention exhibit substantially reduced skin irritation compared to a chlorine dioxide generating composition which does not contain one or more of these specific skin irritation compounds.

DETAILED DESCRIPTION OF THE INVENTION

The term "salt of a chlorite" or "chlorite salt" is used throughout the specification to describe a salt of chlorite which is readily soluble in an aqueous system and which readily dissociates into chlorite anion and counterion (generally, metal). Two particularly preferred salts of chlorites for use in the present invention include sodium chlorite and potassium chlorite.

The term "acid" is used throughout the specification to describe protic acids, i.e., acids that release hydrogen ions in solution. Acids for use in the present invention include strong inorganic acids which are diluted for application to the skin such as for example, hydrochloric, sulfuric, sulfamic and nitric acid, preferably as dilute acid, organic acids such as citric, fumaric, glycolic, lactic, malic, mandelic and tartaric acid, among others. Preferred acids include sodium and potassium bisulfate ($NaHSO_4$ and $KHSO_4$), phosphoric acid, mandelic acid, tartaric acid and maleic acid.

The term "low pKa acid" is used throughout the specification to describe acids which are relatively strong (have pKa's of about 2.1 or lower, preferably below about 1.94, the pKa of chlorous acid so as to shift the equilibrium to chlorous acid generation) and are easily or relatively safely handled, are generally compatible with biological systems (they are substantially non-toxic) and are non-caustic. Low pKa acids donate a large fraction of hydrogen ions by favoring the reaction which consumes hydrogen ions and generates chlorine dioxide. By virtue of the low pKa, the acids utilized in the present invention are highly ionized and smaller quantities of the low pKa acid would be needed to protonate chlorite ions to form chlorous acid compared to higher pKa acids. Consequently, the acids have low residual levels and the mixture is easily raised in pH when touching skin or disinfecting an instrument.

In the present invention, the use of a low pKa acid preferably used within a range of pH of about 2.75 to about 4.5 (more preferably, about 3.0 to about 4.0 within this range) in combination with a salt of chlorite to generate chlorine dioxide is preferred and is consistent with the substantial absence of the free acid form of the low pKa acid in solution. The substantial absence of the free acid form is preferred because it makes the reduction in irritation easier to obtain; first, because less acid is needed to produce a particular pH, and second, because at a particular pH, less acid will be in a protonated form, which has a greater likelihood of penetrating the skin and producing further irritation (in addition to that produced by the chlorine dioxide).

Examples of preferred acids for use in the present invention include sodium and potassium bisulfate ($NaHSO_4$ and $KHSO_4$), phosphoric acid, maleic acid, mandelic acid and tartaric acid. The bisulfates have pKa's of about 1.9–2.0, phosphoric acid has a pKa of about 2.15 and maleic acid has a pKa of about 1.94. Other biologically compatible acids which may be used in the present invention include ethylenediaminetetraacetic acid (EDTA, as the free acid or the monosodium salt), among others.

The term "substantial quantity" is used to describe amounts of chlorine dioxide which are produced using the method according to the present invention and are believed to be useful. A substantial quantity of chlorine dioxide for purposes of the present invention is at least about 1 part per million produced in a period of time no greater than about 15 minutes, because chlorine dioxide is a disinfectant at that concentration and higher concentrations. In the present invention, chlorine dioxide is preferably produced in a concentration of at least about 5 parts per million after about a 15 minute period, more preferably in a concentration of at least about 10–20 parts per million after said 15 minute period. Concentrations of chlorine in excess of 50 parts per million or higher may be obtained using the chlorine dioxide formulations according to the present invention. Each of these formulations which contains an effective amount of an irritation reducing compound selected from the group consisting of allantoin, glycerine, aloe vera and mixtures, thereof, unexpectedly substantially reduces irritation compared to compositions which do not contain an irritation reducing compound according to the present invention.

The term "irritation reducing compound" is used throughout the specification to describe a compound which, when included in chlorine dioxide generating compositions according to the present invention substantially reduces the irritation which is produced by chlorine dioxide when it comes into contact with mammalian skin. Irritation reducing agents for use in the present invention include allantoin, glycerine, aloe vera and mixtures thereof.

The term "allantoin" is used throughout the specification to describe one of the irritation reducing compounds which are included in compositions according to the present invention. Allantoin (also known as (2,5-Dioxo-4-imidazolidinyl)urea, 5-ureidohydantoin, glyoxyldiureide, cordianine, psoralon, or septalan) is a well-known product of purine metabolism. It is generally prepared synthetically by the oxidation of uric acid with alkaline potassium permanganate.

The term "glycerine" is used throughout the specification to describe another of the irritation reducing compounds which are included in compositions according to the present invention. Glycerine (also known as glycerol, trihydroxypropane, incorporation factor, IFP or ophthalgan) is a well-known cosmetic and pharmaceutical additive obtained from oils and fats as a by-product of the manufacture of soaps and fatty acids. It is quite surprising that this composition may be utilized with a great deal of success in chlorine dioxide formulations according to the present invention because it is contraindicated to use glycerine in combination with a strong oxidizing agent because of the stability concerns raised.

The term "aloe vera" is used throughout the specification to describe a complex compositional mixture obtained from dried latex of leaves of Curacao Aloe or Cape Aloe. Aloe vera contains approximately 18–25% by weight aloin (Curacao) or 4–5% aloin (Cape), and further contains resin, emodin and volatile oil. Aloe vera for use in the present invention may be obtained from a number of manufacturers/distributors including Aloe Corporation. The term aloe vera used to describe the present invention is the same term well known in the cosmetic industry to describe the complex mixture obtained from the Aloe leaves.

The term "substantial absence" or "substantially reduce" is used throughout the specification to describe the reduction in irritation that skin exposed to chlorine dioxide compositions according to the instant invention will exhibit compared to virtually identical chlorine dioxide compositions which do not contain an irritation reducing compound according to the present invention. In preferred embodiments according to the present invention, the skin exposed to the present compositions will evidence an absence of reddening, itching and sensitivity associated with the topical administration of chlorine dioxide. This is an unexpected result.

The term "chlorite part" is used throughout the specification to describe the form in which an amount of a water soluble salt of chlorite either in dry or liquid state, alone or in combination with other components, is added to an acid part to produce chlorine dioxide.

The term "acid part" is used throughout the specification to describe the form in which an amount of a water soluble acid either in dry or liquid state, alone or in combination with other components, is added to the chlorite part to generate chlorine dioxide.

In generating chlorine dioxide, effective amounts of an aqueous soluble salt of chlorite is combined with an acid at a pH within the range of about 3.0 to about 4.5 to generate at least about 1 part per million (ppm) of chlorine dioxide within a period of time of no greater than about 15 minutes.

The overall pH range for purposes of the present invention is from less than about 2.75 to about 5.0, preferably about 2.75 to about 4.5, more preferably about 3.0 to about 4.0. In the case of gel formulations, the pH ranges from slightly less than about 3.0 to about 4.5.

The term "effective amount" is used throughout the specification to describe a minimum amount, quantity or concentration of a component, i.e., an acid (preferably, a low pKa acid as described herein), an aqueous soluble chlorite salt or an irritation reducing compound, included to generate an intended effect, i.e., a concentration of chlorine dioxide of about 1 ppm generated within a period about 10 minutes which evidences substantially reduced irritation (preferably, a substantial absence of irritation) compared to compositions which do not contain effective amounts of irritation reducing compounds. The term effective amount when used to describe the acid, preferably a low pKa acid, is used to describe that amount of acid, either in dry or liquid form which, when combined with chlorite in solution, will generate a desired concentration of chlorine dioxide, i.e., at least about 1 part per million (ppm) and preferably at least about 5 ppm of chlorine dioxide within a period of no greater than about 10 minutes. By definition, 1 part per million is equal to 0.0001% by weight.

In the case of the inclusion of an irritation reducing compound in compositions according to the present invention, an effective amount may preferably range from about 0.05% to about 50% by weight of the final composition which generates chlorine dioxide. In the case of aloe vera, the amount included in compositions according to the present invention ranges from about 0.1 to about 10%, more preferably about 0.5% to about 1.5%. In the case of allantoin, this compound is included in an amount ranging from about 0.05 to 10%, more preferably within the range of about 0.25 to about 3.0%. In the case of glycerine, this compound is generally included in an amount ranging from about 0.5% to about 50% by weight of the present compositions. Although the above-described weight ranges may be used as general guidelines for the inclusion of irritation reducing compounds in the present compositions, one of ordinary skill in the art will recognize to vary the weight ratio of aloe vera, allantoin and/or glycerine within the teachings of the present invention to produce chlorine dioxide compositions which evidence substantially reduced irritation compared to prior art formulations.

The term "gel composition" or "gel" is used to describe an aqueous composition according to the instant invention which includes an amount of a gelling agent effective for gelling the composition. Gel compositions are preferred for topically delivering chlorine dioxide to a site in need of disinfection or chlorine dioxide therapy. In general, the amount of a gelling agent included in the aqueous chlorine dioxide generating compositions according to the present invention ranges from about 0.5% to about 5–6% (or more) by weight of the composition, with a preferred amount of gelling agent falling within the range of about 1% to about 4% by weight.

Gelling agents for use in the present invention include, for example, natural and synthetic gelling agents including polysaccharides extracted from plants. Other gelling agents include high molecular weight polyoxyalkylene crosslinked acrylic polymers as well as the highly preferred cellulosics such as hydroxymethyl cellulose, hydroxypropyl cellulose, hydroxyethyl cellulose, among others including high molecular weight polyethylene glycols, polyvinyl alcohol-boric acid gels, polyacrylamide gels and crosslinked polyvinylpyrrolidones, among others. The gelling agents according to the present invention generally are sterilized prior to inclusion in the instant formulations. It is preferred that the gelling agent should be stable to pH's ranging from less than about 2 to greater than about 10 so that they can be used in all formulations (including a chlorite part and acid part which are mixed to generate chlorine dioxide).

Compositions according to the present invention relate to the unexpected discovery that the inclusion of effective amounts of an irritation reducing compound selected from the group consisting of allantoin, glycerine, aloe vera and mixtures, thereof, in a chlorine dioxide generating composition will substantially reduce skin irritation which is caused by chlorine dioxide exposure to the skin in comparison to compositions which do not contain (contain an absence of) such an irritation reducing component.

Typically, if an acne or herpes lesion is treated with a standard $ClO_2$ gel, there would probably be no irritation produced at the first application. However, if the gel is used a second time within 24 hours, which is often necessary for the disease reduction process, the sore and area around the sore would often get red and sensitive, even though the infection would be greatly lessened. When the protective additives are part of the gel formulation, this reddening on the second, or further applications, is greatly reduced or prevented entirely.

Compositions according to the present invention comprise an aqueous soluble salt of chlorite in combination with a protic acid, the salt of chlorite and acid being included in the composition in amounts effective to generate at least about 1 part per million (ppm), preferably at least about 5 ppm, more preferably at least about 10–20 ppm and up to about 50 ppm or more chlorine dioxide within a period of time no greater than about 15 minutes, the composition also including water and at east one irritation reducing compound selected from the group consisting of allantoin, glycerine, aloe vera and mixtures, thereof, in an amount effective to substantially reduce skin irritation caused by chlorine dioxide. The compositions according to the present invention exhibit substantially reduced skin irritation compared to a chlorine dioxide generating composition which does not contain one or more of these specific skin irritation compounds. In preferred embodiments, the compositions according to the present invention evidence a substantial absence of irritation (i.e., redness and itchiness) of the skin.

In one aspect of the present invention, a gel matrix is described. Gel compositions are preferred for use as topical chlorine dioxide producing compositions. The gel matrix according to the present invention is intended for use on mammalian skin, preferably human skin, as a delivery vehicle for chlorine dioxide. In the present invention, the use of certain irritation reducing compounds in combination with those which are directly responsible for the production of chlorine dioxide according to the instant invention are particularly useful in a gel matrix for delivering chlorine dioxide. Gel. compositions according to the present invention are produced in an aqueous system.

The present invention which relates to a topical gel formulation preferably utilizes a low pKa acid selected from the group consisting of an aqueous soluble bisulfate salt, maleic acid, phosphoric acid, ethylenediaminetetracetic acid, monosodium ethylenediaminetetracetic acid and mixtures thereof and an aqueous soluble salt of chlorite in combination with an irritation reducing agent selected from the group consisting of aloe vera, allantoin, glycerine and mixtures, thereof at an initial pH ranging from about 2.75 to about 4.5. This combination of additives in aqueous solution is combined with a gelling agent, the gelling agent being included in an amount effective to produce a gel for topical delivery of the formulation. This combination of ingredients as disclosed herein at an initial pH of about 2.75–3.0 to about 4.5 is consistent with the formation and delivery of concentrations of chlorine dioxide of at least about 1 ppm, preferably at least about 5 ppm, more preferably at least about 10–20 ppm and as much as about 50 ppm or more for topical applications. While acids other than low pKa acids may be used, the low pKa acids are clearly preferred for use in the present gel formulations.

In addition to effective amounts of acid, chlorite salt, irritation reducing agent, water and gelling agent, the gel formulations according to the present invention advantageously employ numerous additives which are commonly used in cosmetic and pharmaceutical formulations. These additives include, for example, surfactants such as sodium lauryl sulfate and poloxamer™ (polyoxypropylene/polyoxyethylene block copolymer), among numerous others, emulsifiers, appropriate wound healing agents, diluents and fillers such as ethyl alcohol and isopropyl alcohol and humectants such as propylene glycol. These additives are generally included in amounts ranging from about 0.025% to about 8% by weight or more. Fragrances also may be advantageously employed in amounts ranging from about 0.01% to about 1% by weight or more.

In addition to exhibiting a substantial absence of skin irritation, compositions according to the present invention in many instances unexpectedly evidence enhanced skin penetration of the chlorine dioxide produced.

Compositions according to the present invention may be used in a wide variety of applications for treating mammalian skin where the use of chlorine dioxide is desirable. Applications which rely on the disinfectant properties of chlorine dioxide on the skin are especially preferred.

EXAMPLES

The following examples are provided to illustrate the present invention and should not be construed to limit the scope of the invention of the present application in any way.

Example 1

Skin Protectant Composition

|  | gram w/w % |
|---|---|
| PART (A) Chlorite Part-Including Glycerine and Allantoin | |
| Hydroxyethyl cellulose | 2.475 |
| Glycerine | 4.000 |
| Sodium chlorite (80%) | 2.000 |
| Sodium Hydroxide (10N) | 0.400 |
| Ethyl alcohol | 5.000 |
| Allantoin | 5.000 |
| Fragrance | 0.027 |
| Water | q.s. |
| PART (B) Acid Part | |
| Hydroxyethyl cellulose | 2.400 |
| Glycerine | 8.000 |
| Potassium bisulfate | 0.825 |
| Ethyl alcohol | 6.000 |
| Allantoin | 0.500 |
| Fragrance | 0.027 |
| Water | q.s. |

Directions for use: Mix equal amounts of Part (A) and Part (B) just before use.

Example 2

Skin Sanitizing Liquid Composition

|  | gram w/w % |
|---|---|
| PART (A) Chlorite Part- | |
| Sodium chlorite (80%) | 0.400 |
| Water | 99.200 |
| Sodium Hydroxide (1N) | Adjust formulation to pH 10.6 |
| PART (B) Acid Part Using Aloe Vera | |
| Aloe Vera | 0.500 |
| Potassium bisulfate | 7.480 |
| Water | q.s. |

Directions for use: Mix equal amounts of Part (A) and Part (B) just before use.

This invention has been described in terms of specific embodiments set forth in detail herein, but it should be understood that these are by way of illustration and the invention is not necessarily limited thereto. Modifications and variations will be apparent from the disclosure and may be resorted to without departing from the spirit of the inventions those of skill in the art will readily understand. Accordingly, such variations and modifications are considered to be within the purview and scope of the invention and the following claims.

We claim:

1. A method of producing chlorine dioxide on mammalian skin comprising:
   (a) combining in an aqueous solution an aqueous soluble chlorite salt and an aqueous soluble acid, said chlorite salt and said acid being included in said solution in concentrations effective to produce chlorine dioxide in a concentration of at least about 1 part per million after a period of no greater than about fifteen minutes, said solution having an initial pH ranging from about 2.75 to about 4.5 and further including at least one irritation reducing compound selected from the group consisting of aloe vera, allantoin, glycerins and mixtures thereof in an amount effective to substantially reduce skin irritation associated with the exposure of mammalian skin to said solution; and (b) applying said solution from step (a) to mammalian skin.

2. The method according to claim 1 wherein said irritation reducing composition is included in said solution in an amount ranging from about 0.05% to about 50% by weight of said solution.

3. The method according to claim 2 wherein said irritation reducing compound is aloe vera in an amount ranging from about 0.1% to about 10% by weight of said solution.

4. The method according to claim 2 wherein said irritation reducing compound is allantoin in an amount ranging from about 0.05% to about 10% by weight of said solution.

5. The method according to claim 2 wherein said irritation reducing compound is glycerine in an amount ranging from about 0.5% to about 50% by weight of said solution.

6. The method according to claim 1 wherein said acid is selected from the group consisting of aqueous soluble bisulfate salts, maleic acid, mandelic acid, tartaric acid, phosphoric acid, ethylenediaminetetraacetic acid, monosodium ethylenediaminetetraacetic acid and mixtures thereof.

7. The method according to claim 1 wherein said chlorite salt is selected from the group consisting of sodium chlorite potassium chlorite and mixtures, thereof.

8. The method according to claim 1 wherein said solution further includes an amount of a gelling agent effective to gel said solution.

9. The method according to claim 8 wherein said gelling agent is selected from the group consisting of hydroxymethyl cellulose, hydroxyethyl cellulose, hydroxypropyl cellulose and mixtures thereof.

10. The method according to claim 8 wherein said solution further includes at least one additive selected from the group consisting of surfactants, emulsifiers, wound healing agents, lubricants, film-formers, diluents, fillers and humectants.

11. The method according to claim 1 wherein said aqueous solution has an initial pH of about 3.0 to 4.5.

12. A method of producing chlorine dioxide on mammalian skin comprising:

(a) combining in an aqueous solution an aqueous soluble chlorite salt selected from the group consisting of sodium chlorite and potassium chlorite and an aqueous soluble acid selected from the group consisting of aqueous soluble bisulfate salts, maleic acid, mandelic acid, tartaric acid, phosphoric acid, ethylenediaminetetraacetic acid, monosodium ethylenediaminetetraacetic acid and mixtures thereof, said chlorite salt and said acid being included in said solution in concentrations effective to produce chlorine dioxide in a concentration of at least about 1 part per million after a period of no greater than about ten minutes, said solution having an initial pH ranging from about 2.75 to about 4.5 and further including at least one irritation reducing compound selected from the group consisting of aloe vera, allantoin, glycerins and mixtures thereof in an amount effective to substantially reduce skin irritation after application of said solution to the skin; and (b) applying said solution from step (a) to mammalian skin.

13. The method according to claim 12 wherein said irritation reducing composition is included in said solution in an amount ranging from about 0.05% to about 50% by weight of said solution.

14. The method according to claim 13 wherein said irritation reducing compound is aloe vera in an amount ranging from about 0.1% to about 10% by weight of said solution.

15. The method according to claim 13 wherein said irritation reducing compound is allantoin in an amount ranging from about 0.05% to about 10% by weight of said solution.

16. The method according to claim 13 wherein said irritation reducing compound is glycerine in an amount ranging from about 0.5% to about 50% by weight of said solution.

17. The method according to claim 12 wherein said aqueous solution further includes an amount of a gelling agent effective to gel said solution.

18. The method according to claim 17 wherein said gelling agent is selected from the group consisting of hydroxymethyl cellulose, hydroxyethyl cellulose, hydroxypropyl cellulose and mixtures thereof.

19. The method according to claim 17 wherein said solution further includes at least one additive selected from the group consisting of surfactants, emulsifiers, wound healing agents, lubricants, film-formers, diluents, fillers and humectants.

20. An aqueous substantially non-irritating chlorine dioxide generating composition comprising an aqueous solution made by mixing an aqueous soluble chlorite salt selected from the group consisting of sodium chlorite and potassium chlorite and an aqueous soluble acid selected from the group consisting of aqueous soluble bisulfate salts, maleic acid, mandelic acid, tartaric acid, phosphoric acid, ethylenediaminetetraacetic acid, monosodium ethylenediaminetetraacetic acid and mixtures thereof in water, said chlorite salt and said acid being included in said solution in concentrations effective to produce chlorine dioxide in a concentration of at least about 1 part per million after a period of no greater than about ten minutes after said mixing, said solution having an initial pH after mixing ranging from about 2.75 to about 4.5 and further including at least one irritation :reducing compound selected from the group consisting of aloe vera, allantoin and mixtures thereof in an amount effective to substantially eliminate skin irritation associated with the exposure of said composition to mammalian skin, said aloe vera being included in said composition in an amount ranging from about 0.1% to about 10% by weight of said solution and said allantoin being included in said composition in an amount ranging from about 0.05% to about 10% by weight of said composition.

21. The composition according to claim 20 wherein said solution further includes an amount of a gelling agent effective to gel said solution.

* * * * *